United States Patent
Kim et al.

(10) Patent No.: US 10,347,370 B1
(45) Date of Patent: Jul. 9, 2019

(54) DERIVING A PATIENT LEVEL LONGITUDINAL DATABASE FOR RAPID CYCLE ANALYTICS

(71) Applicant: Aetion, Inc., New York, NY (US)

(72) Inventors: Peter S. Kim, Manhattan Beach, CA (US); Francis Hill Fung Lam, New York, NY (US); Jeremy A. Rassen, New York, NY (US); Allon E. Rauer, New York, NY (US); Sebastian Schneeweiss, Newton, MA (US)

(73) Assignee: AETION INC., New York, NY (US)

( * ) Notice: Subject to any disclaimer, the term of this patent is extended or adjusted under 35 U.S.C. 154(b) by 724 days.

(21) Appl. No.: 14/828,113

(22) Filed: Aug. 17, 2015

(51) Int. Cl.
*G06F 16/2455* (2019.01)
*G16H 10/60* (2018.01)
*G06F 16/13* (2019.01)
*G06F 16/9537* (2019.01)

(52) U.S. Cl.
CPC ............ *G16H 10/60* (2018.01); *G06F 16/13* (2019.01); *G06F 16/24568* (2019.01); *G06F 16/9537* (2019.01)

(58) Field of Classification Search
CPC .. G06F 19/322; G06F 19/3493; G06F 19/328; G06F 17/30091; G06F 17/30516; G06F 16/24568
USPC ............................................................. 705/3
See application file for complete search history.

(56) References Cited

U.S. PATENT DOCUMENTS

| | | | |
|---|---|---|---|
| 5,787,414 A * | 7/1998 | Miike | G06F 17/30017 707/796 |
| 8,140,562 B1 | 3/2012 | Kuraoka et al. | |
| 8,370,597 B1 | 2/2013 | Chatterjee et al. | |
| 2005/0154710 A1 | 7/2005 | Ruhlow et al. | |
| 2006/0059187 A1 | 3/2006 | Brown | |
| 2006/0161557 A1 | 7/2006 | Dettinger et al. | |
| 2007/0239508 A1 | 10/2007 | Fazal et al. | |
| 2008/0010254 A1* | 1/2008 | Settimi | G06Q 10/06 |
| 2008/0091638 A1 | 4/2008 | Suzuki | |
| 2009/0299676 A1 | 12/2009 | Michon et al. | |
| 2009/0299767 A1 | 12/2009 | Michon et al. | |

(Continued)

OTHER PUBLICATIONS

USPTO Non-Final Office Action for U.S. Appl. No. 14/083,406 dated Aug. 18, 2015, 19 pages.

(Continued)

*Primary Examiner* — Hiep V Nguyen
(74) *Attorney, Agent, or Firm* — Lowenstein Sandler LLP

(57) ABSTRACT

In one embodiment, a method of assembling a longitudinal database is provided. The method comprises receiving, using a processor of a data storage unit, medical data streams from a plurality of sources. The medical data streams include patient data related to a plurality of medical events. A first date range that indicates a time span associated with the patient is identified in view of the patient data. The medical events are normalized into a plurality of linking keys based on the first date range. The keys are adapted to longitudinally link each medical event in a sequence of occurrence. Each key of comprises an offset from a start date of the first date range for a corresponding medical event. The medical events are compressed in view of the keys. The compressing generates a location index for each medical event associated with the keys based on a corresponding offset.

20 Claims, 13 Drawing Sheets

(56) References Cited

U.S. PATENT DOCUMENTS

| | | |
|---|---|---|
| 2010/0114900 A1 | 5/2010 | Anderson |
| 2011/0301982 A1* | 12/2011 | Green, Jr. ............ G06F 19/3443 |
| | | 705/3 |
| 2013/0173306 A1 | 7/2013 | Sasidhar |
| 2015/0142821 A1 | 5/2015 | Rassen et al. |

OTHER PUBLICATIONS

USPTO Final Office Action for U.S. Appl. No. 14/083,406 dated Feb. 5, 2016, 21 pages.

* cited by examiner

700

OPERATORS

| Example Syntax V(t) | Return Type |
|---|---|
| PatientAttribute<T>(t) | T |
| First(V<T>, D(t)) | T |
| Last(V<T>, D(t)) | T |
| Exists(V<T>, T, D(t)) | Bool |
| AllEquals(V<T>, T, D(t)) | Bool |
| Collapse(EventSet, EventAttribute<T>) | T |
| CountUnique(EventSet, EventAttribute<T>, D(t)) | Int |
| Count(V<Bool>, D(t)) | Int |
| Sum(V<Int>, D(t)) | Int |
| Sum(V<Float>, D(t)) | Float |
| Active(V<Bool>, V<Int>) | Bool |
| Extend(V<Bool>, V<Int>) | Bool |
| Bound(V<Int>, V<Int>, V<Int>) | Int |
| InInterval(V<Int>, V<Int>, V<Int>) | Bool |
| Categorize((V<Bool> => Enum)[]) | Enum |
| Score(V<Enum>, (Enum => Float)[]) | Float |
| Flipped(V<Bool>, Bool) | Bool |
| Not(V<Bool>) | Bool |
| And(V<Bool>[]) | Bool |
| Or(V<Bool>[]) | Bool |
| Add(V<Int>[]) | Int |
| Add(V<Float>[]) | Float |
| Square(V<Int>) | Int |

DERIVING A PATIENT LEVEL LONGITUDINAL DATABASE FOR RAPID CYCLE ANALYTICS

TECHNICAL FIELD

Embodiments of the present disclosure relate generally to database systems, and more specifically, to techniques for deriving a patient level longitudinal database for rapid cycle analytics.

BACKGROUND

Many organizations collect large amounts of patient event data related to activities for treating a patient for various medical conditions. This patient event data can typically be complex and sparse in time with each event having multiple data attributes, and properties as well as nested sub levels. This complex medical data may come in a variety of forms and is often provided in an unstructured format. Due to the vast amount of complex medical data, current database systems lack the flexibility to effectively handle or assemble such data to provide reproductive or auditable analytics over time.

BRIEF DESCRIPTION OF THE DRAWINGS

The included drawings are for illustrative purposes and serve to provide examples of possible structures and operations for the disclosed inventive systems, apparatus, methods and computer-readable storage media. These drawings in no way limit changes in form and detail to the techniques described herein, which may be made by one skilled in the art without departing from the spirit and scope of the disclosed implementations.

FIG. 7 illustrates a table of operators according to one embodiment.

DETAILED DESCRIPTION

Embodiments of the present disclosure are directed to techniques for deriving a patient level longitudinal database for rapid cycle analytics (RCA). RCA pertains to evidence-based analysis that integrates years of real-world complex medical data including, but not limited to, (a) clinical data, (b) scientific research data and algorithms and (c) patient/caregiver data to predict certain outcomes. For example, the complex medical data may be used to assess the possibility of certain medical outcomes when the patient is already at an elevated condition for that outcome. In other situations, the complex medical data may be analyzed to assess the effectiveness, safety and value of certain treatments as well as other type of outcomes.

Due to the vast volumes of complex medical data involved in RCA, current systems that utilize traditional databases, such as relational database management systems (RDBMS) using structured query languages (SQL) and even Non-SQL, have typically worked on turnaround cycles lasting days or even weeks. One reason for this is that RDBMS is mostly ineffective when processing large amounts of data that have different and expanding sets of properties. Beyond speed, the ability to handle an evidence-based query on complex medical data to assess present and unknown research problems with varying properties requires a flexible big data query language tailored to patient-centric analysis. Embodiments of the present disclosure providing systems and methods that can generate and utilize a highly-compressed longitudinal storage format as well as provide a variable scripting language to deliver improvements in data handling and data query technologies, in ways that are not possible using current database technologies.

I. System Overview

Figure 1:
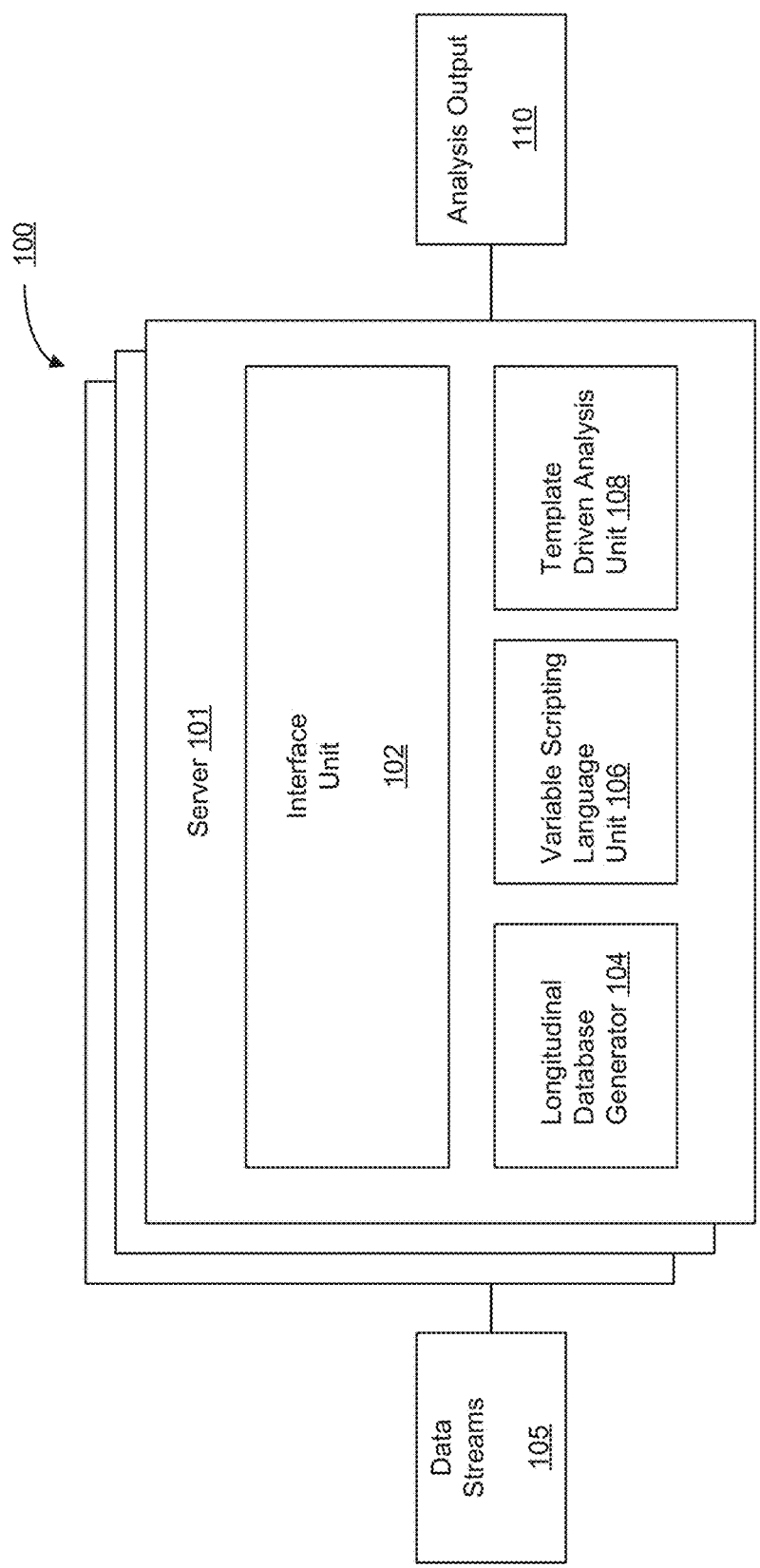
FIG. 1 illustrates a block diagram of a system according to one exemplary embodiment.

FIG. 1 illustrates a block diagram of a system 100, which may be used to support RCA. Although aspects of the disclosure may be particular useful in supporting certain type of systems, this example should not be considered as limiting the scope of the disclosure or usefulness of the features of the present disclosure. For example, the features and techniques described herein can be used with other types of systems where large sets of complex time-oriented data are transformed and analyzed to determine certain outcomes. For example, aspects of the present disclosure may be useful to analyze marketing and sales data related to consumer purchases of products over a given time period in order to predict outcomes regarding, for example, sales and product valuations as well as market trends.

In one embodiment, system 100 includes a plurality of server computing devices, such as server 101. In some embodiments, server 101 may be at one node of network (not shown) and capable of directly and indirectly communicating with other nodes of the network. For example, the server 101 may include a web server that may be capable of communicating with other computing devices of system 100 to transmit and display information via the network. In some embodiments, the plurality of server computing devices may include, e.g., a load balanced cloud-based server farm that exchanges information with different nodes of the network for the purpose of receiving, processing and transmitting data.

To put the RCA capabilities of system 100 into the hands of users (e.g., individuals, industry and academic researches), the users may be provided with a variety of different interfaces. In one embodiment, server 101 may include an interface unit 102. The interface unit 102 may be adapted to facilitate various types interaction with system 100 that may include data queries and business work-flows (e.g., reporting and research data analysis) supported by the system 100. In some embodiments, the interface unit 102 may include components that allow users to collaborate, share and/or access data from a variety of sources and retrieve outcome analyses provided by system 100. In one embodiment, the interface unit 102 may include an application (e.g., a web application) associated with server 101 for accessing system 100. The users may have to install the application and/or select a service in order to obtain the benefits of the techniques described herein. The application may be installed locally at a client computing device (not shown) associated with the users. Alternatively, the application can be stored at the service and may be accessed using the client computing device, for example, via a web browser.

In order to facilitate operations of system 100 for supporting RCA, the server 101 may further include several modules, such as a longitudinal database generator 104 to access and transform massive volumes of input data streams 105 (e.g., patient data) from any format into a time-ordered longitudinal data hierarchy, a variable scripting language unit 106 to make longitudinal searches and select data for analysis from amongst the longitudinal data hierarchy and a template driven analysis unit 108 to perform statistical analyses on the select data and produce analysis output 110 (e.g. data or documentation in a natural language text) that may be presented to the users. The functionally of these modules can exist in a fewer or greater number of modules than what is shown, with such modules residing at one or more computing devices, which may be geographically dispersed. In some embodiments, the modules may be operable in conjunction with other computing devices of system 100 to process and/or analyze data from the longitudinal data hierarchy. Examples illustrating the functionality these modules are further discussed below.

II. Patient Level Longitudinal Database

Figure 2:
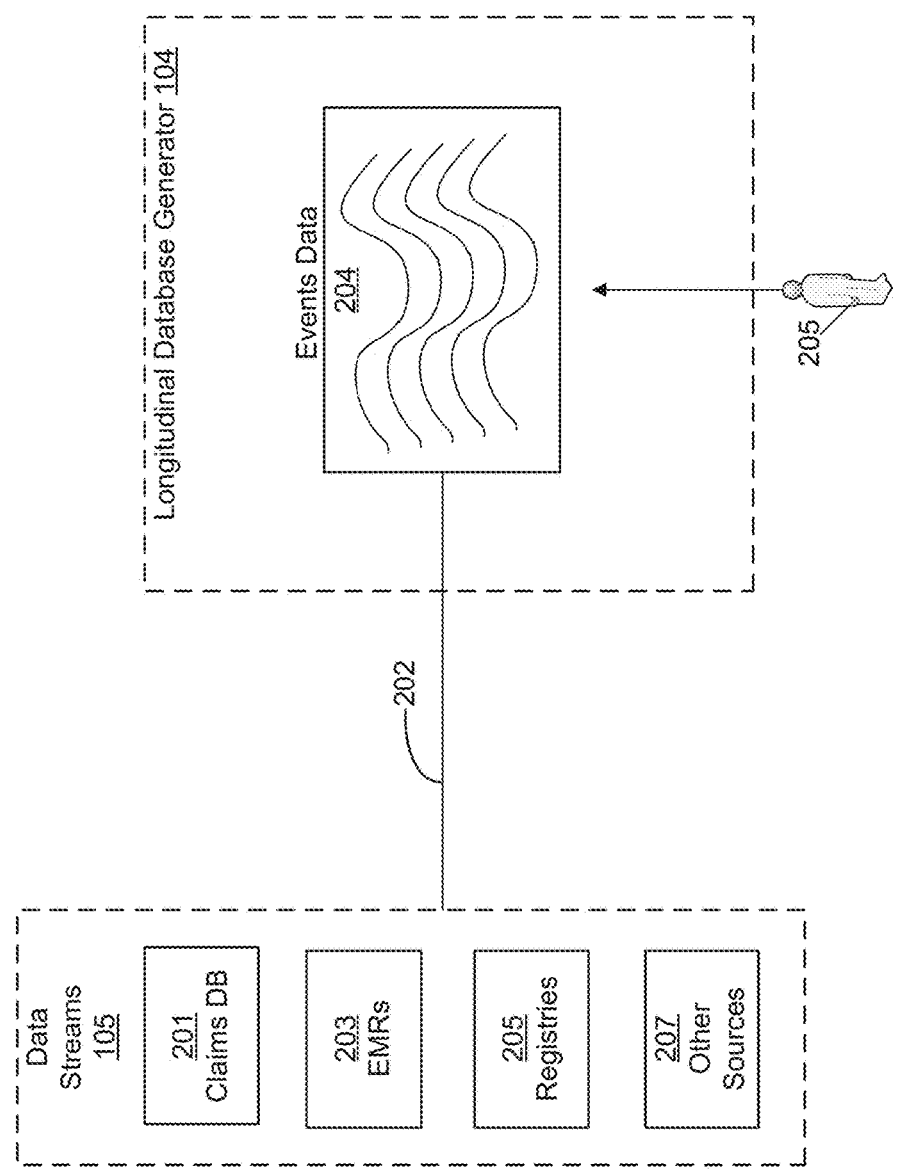
FIG. 2 illustrates a system for assembling a longitudinal database according to one embodiment.

FIG. 2 illustrates a system 200 to support assembling a longitudinal database according to one embodiment. In some embodiments, the system 200 may include longitudinal database generator 104 of FIG. 1. The longitudinal database generator 104 may receive a plurality of data streams 105 comprising data, such as patient medical data. A "patient" may refer to a person who is under medical care or treatment for a medical condition. The data streams 105 may include thousands if not millions of medical records associated with a plurality of patients. In some embodiments, the data streams 105 may be received via a secure connection 202, for example, over a wired or wireless network (not shown). In one embodiment, data files associated with the data streams 105 may be transferred via the secure connection 202 to a staging area before being uploaded into the longitudinal database generator 104. In alternative embodiments, the data files may be sent as physical files, which are then uploaded into the longitudinal database generator 104. The data streams 107 may include events data 204 (e.g., medical events data) associated with a plurality of patients, which may occurred over a given period of time.

Patient medical data associated with the plurality of data streams 107 may be received from a number of sources. These sources may include, for example, claims database (DB) 201 associated with insurance companies, electronic medical records (EMRs) 203 associated with hospitals, physician, clinics and other type of providers, subscription registries 205 that provide medical data for a fee as well as other type of sources 207 of the patient medical data.

Raw patient medical data coming from the different sources can be in a variety of formats and include numerous fields related to the patients. In one embodiment, the longitudinal database generator 106 may identify events data 204 representing medical events associate with a patient 205 by processing this raw data. In some embodiment, the events data 204 may comprise a number of fields that include, but are not limited to, a patient identifier, gender code, race code, birth date, medial event type, such a hospitalization stay, a type of medication taken, prescriptions, a medical event including start and end date of the medical event, sub medial events, treatment plans, outcomes of the treatment plans as well as other relevant data fields. In some embodiments, the fields may be dynamically updated depending on the raw data coming from the different data streams 105.

The plurality of data streams 107 may include a number of sparse events (e.g., medical events) that have occurred over the life of the patient 205. For example, if patient 205 has been alive for forty years (40) that is approximately 14,600 days. During this lifetime, the patient 205 may have had a hundred (100) medical events, which may be located throughout the data streams 107. The medical events may have occurred at any time during those 14,600 days making it hard to do querying and analysis on the data in an effectual manner.

In order to store the medical event data so that queries based on the longitudinal history of the patient 205 may be efficiently employed, the longitudinal database generator 104 may normalize the events data 204 into a data structure that takes into account the life span associated with the patient 206 and a temporal location of where the events have occurred during their life span. Then, this data structure may be compressed and stored in a manner so that it can be used as part of the longitudinal database for supporting RCA.

Figure 3:
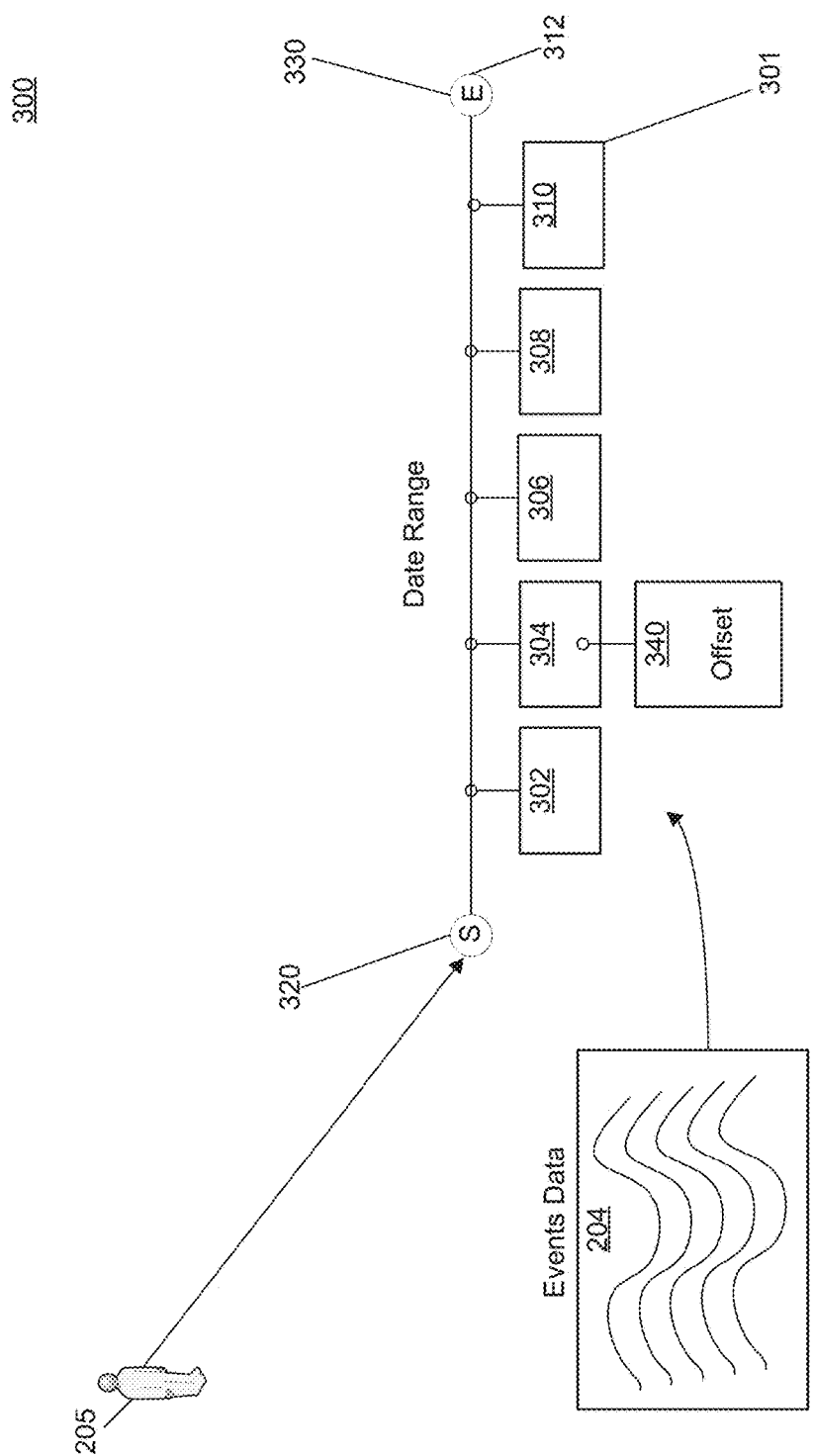
FIG. 3 illustrates a system comprising a data structure according to one embodiment.

In FIG. 3, system 300 comprising a data structure 301 according to one embodiment is shown. In one embodiment, the data structure 301 may comprises a longitudinally linked list having a set of linking keys 302-310. The longitudinal database generator 104 may populate each linking key of the data structure 301, for example, with data from events data 204. As noted above, the events data 204 identifies medical events associated with a patient, such as patient 205. The linking keys 302-310 when taken together may be adapted to represent a sequence of medical events associated with the patient 205. In one embodiment, the medical events may be arranged in a time-ordered sequence of occurrence. In another embodiment, the sequence of occurrence may be in reverse temporal order or an occurrence based on a daily, seasonal, and yearly frequency or arranged in other type of frequencies. In alternative embodiments, the data structure 301 may include, e.g., stacks, arrays, queues and other types of structures that may be used to arrange the sequence of events.

The longitudinal database generator 104 may arrange the linking keys 302-310 with respect to a date range 312. For example, the date range 312 may be identified based on a time span associated with the patient 205, such as a time frame associated with the patient's age. In some embodiments, an indication of the patient's age may be stored in the patient medical data associated with the events data 204. In one embodiment, when the age of the patient 205 is identified, the number of day associated with this age may be used to identify the amount of days within a start date 320 and end date 330 of the date range 312.

In some embodiments, the longitudinal database generator 104 may then expand the number of the linking keys 302-310 such there is linking key for each day in the date range 312. For example, if the patient 205 has been alive for 14000 days, then a linking key is generated for each of those days. Thereupon, data associated with the events data 204 may be placed into a linking key within the date range 312 at a temporal location corresponding to a date that event occurred. For example, if patient 205 has had 400 medical events in their lifetime, data for each of those events are placed in the correct position with in the 14000 linking keys representing days of the lifetime of patient 205.

To optimize the amount of data stored in the linking keys 302-310, each key may be associated with an offset, such as offset 340. The offset 340 may represent a difference between the amount of days from the start date 302 and the date that a corresponding event occurred. For example, if patient 205 was born on Jan. 1, 1975, and had a medical event on their birthday in 1978, then instead of storing at linking key 304 that and event happened on that date the offset 340 to 1095 days. This indicates that a medical event happened 1095 days (e.g., 365 days*3) from start date 320. An advantage of optimizing the linking keys 302-310 is this manner is to minimize the amount of storage space used by the keys, for example, storing the number 1095 would require few bits than storing the date Jan. 1, 1978.

Figure 4:
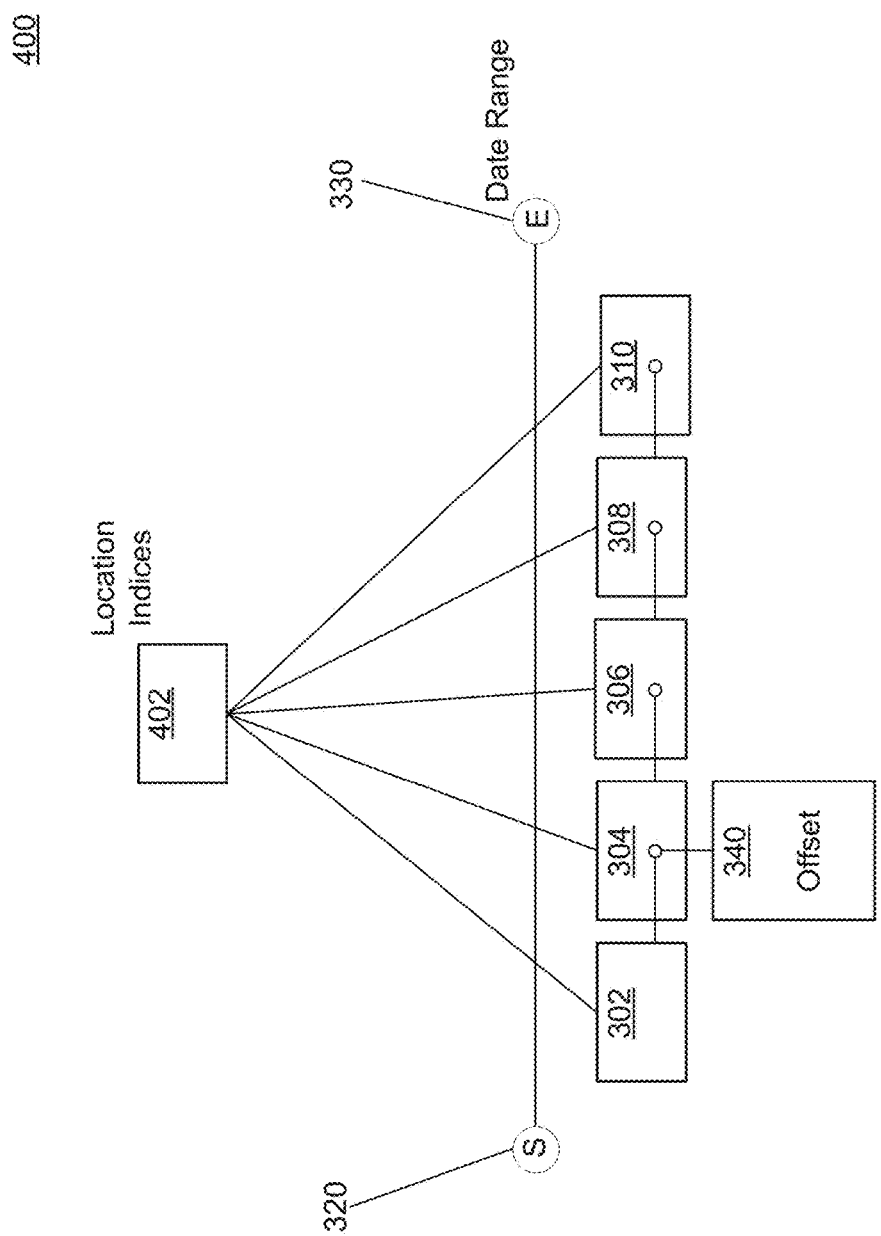
FIG. 4 illustrates a data structure used for compressing events data according to one embodiment.

To reduce the amount of unused space that may be created by expanding the events data 204, the events data 204 associated with the linking keys 302-310 is further compressed by extracting certain information. In FIG. 4, an illustration 400 of a data structure 402 used for compressing events data is shown. In this example, the data structure 402 may be used to identify the temporal locations for each of the linking keys 302-310. For example, when the linking keys 302-310 are compressed, header or metadata information may be extracted and used as a type of location index to identify data points in date range 312 that are of high interest. The header information may act like a location index so that specific event data can be quickly plucked out of the event data history. In some embodiments, various kinds of compression algorithms can be utilized to compress linking keys 302-310. These compression algorithms may include, for example, LZ4, GZIP, Snappy and other types of compression algorithm that can be used in analyzing data to identify high interest data. After the medical event data is compressed, at least of portion of this data may be stored.

Figure 5:
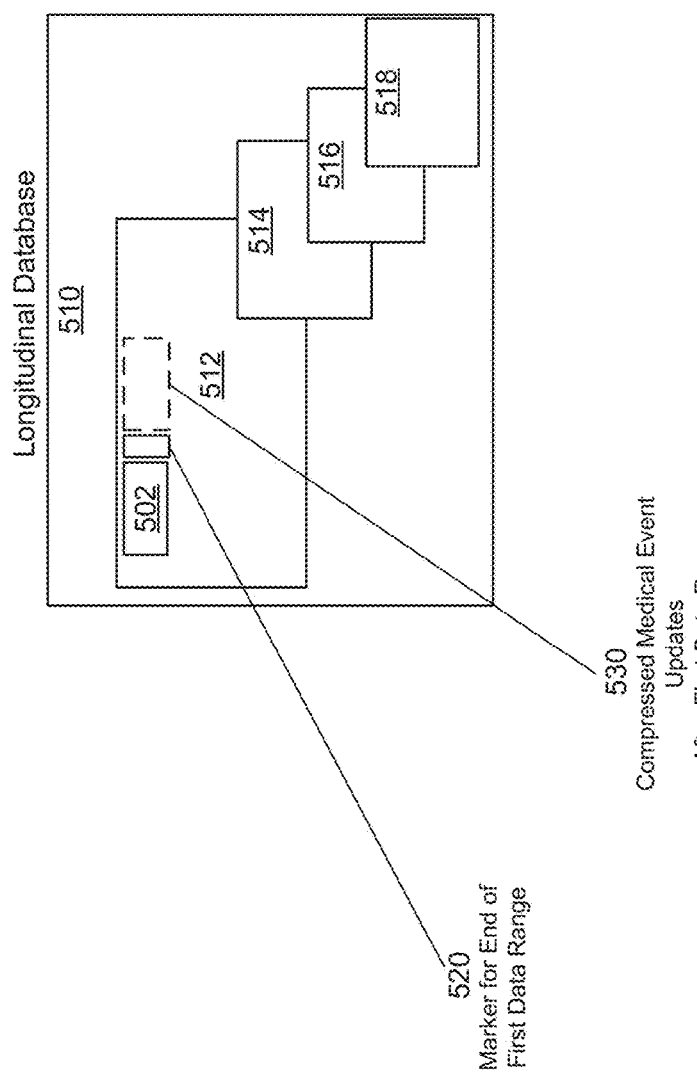
FIG. 5 illustrates a system comprising a storage unit according to one embodiment.

In FIG. 5, a storage unit 500 to support assembling a longitudinal database 510 according to one embodiment is shown. In one embodiment, the longitudinal database 510 may include a file system that comprises a set of files 512-518 stored electronically. The file system uses the files 512-518 for storing information in an encrypted format using various encryption techniques. The files 512-518 are encrypted to protect them from access by unauthorized applications. In some embodiments, medical event data 204, linking keys 302-310, location indices 402 may be stored at a location 502 within a file 512 of file system 510 and used to support the RCA capabilities of system 100.

When new patient data is received, the storage unit 500 may be updated in a manner so as to preserve a state of the data before the new data arrived. For example, if event data in the storage unit 500 is from 2009 to 2014 and then 2015's data comes in, data between 2014 and 2015 is store in way so as to preserve accessing the longitudinal database 510 without the inclusion of the 2015 data. In one embodiment, a new delta of event data between the old data and new data is generated. This delta is normalizes and compressed as disused above, and then stored in a different location, such as location 530. Thereupon, the old data at location 502 can be accessed as if new data at location 530 never came in. Alternatively, only the new data at location 530 can be accessed by filtering out the data at location 502.

To facilitate the filtering of old and new data stored in the file system 510, a marker 520 may be used to indicate a border between the old and new data. For example, the marker 520 may be associated with an end date of the first date range for the events data stored at location 502. In some embodiments, an additional marker, such as marker 520, may be stored each time a new set of event data comes in. Each marker may be used to indicate a new date range of event data added to the file system 510. Thus, if a user is running an analysis query on data in the longitudinal database 510 on the file system, the analysis may be assured to include event data only from a certain date range based on the marker 520 associated with that date range.

III. Patient Variable Language

A file system typically has no standard data query mechanism for searching for specific data items within files managed by the file system. Embodiments of the present disclosure provide a variable scripting language unit 106 for constructing complex longitudinal searches on the medical events data stored in the file system of storage unit 500. The variable scripting language unit 106 is designed to interact with the file system to facilitate the identification and transfer of data from the longitudinal database 510. In some embodiments, the variable scripting language unit 106 allows users to select longitudinal event data sets for a patient or set of patient for analysis, such as for RCA.

Figure 6:
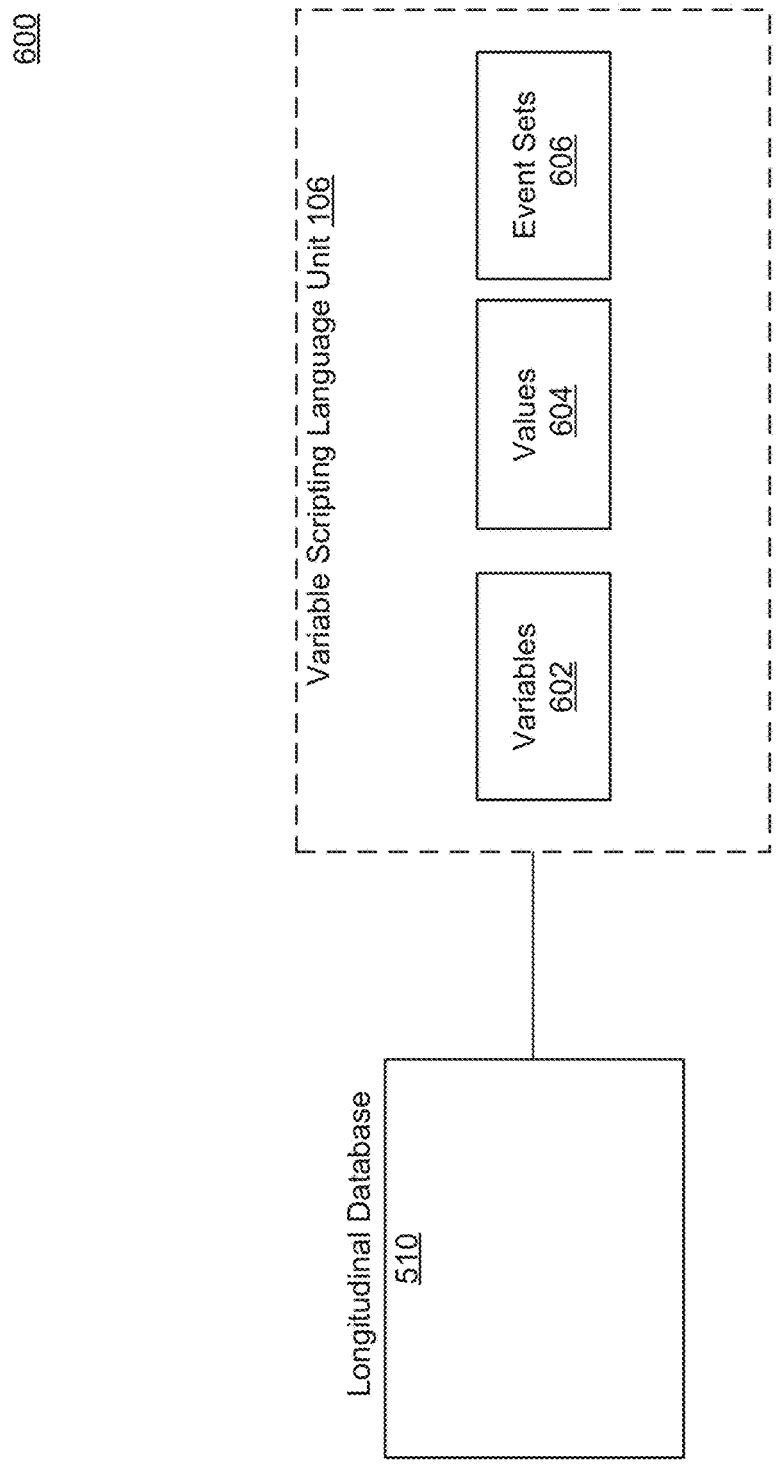
FIG. 6 illustrates a system for analyzing patient level longitudinal event data according to one embodiment.

Turning to FIG. 6, a system 600 for analyzing patient level longitudinal event data according to one embodiment is shown. In one embodiment, the system 600 includes variable scripting language unit 106 of system 100. The variable scripting language unit 106 is able to construct complex, time-varying medical queries from the underlying patient data events. As noted above, patient data events are typically sparse in time and each event can have multiple data attributes as well as other nested events.

For RCA, certain patient events need to be measured according to particular algorithm for a determined set of days. Depending on many different sets of events that have occurred at any point in time, complex operations may be required on those events to get to a final result or predicted outcome. In some embodiments, the variable scripting language unit 106 can represent these complex inputs and dependencies as a set of operations, which can be flexibly composed to construct the logic to derive these final results.

The variable scripting language unit 106 operates on the following data types: variables 602 and values 604 and event sets 606. Variables 602 are a time series of values of, e.g., Boolean, integer, double, category, or string sets types. In some embodiments, the variables 602 are created as a result of operating on event sets 606 to pull out specific attributes or exposure certain event characteristics. Values 604 are measured from variables 602 as a value on a single date, or an aggregation of values over days. The values 604 include data used for per patient information, such as in patient characteristics, predictive outcomes, cohort inclusions, e.g., a group of patients having a statistical factor in common, etc. Event sets 606 are time ordered lists of events selected from the longitudinal database 510 generated from the patient data streams. Each event set has a start and end date and may also have many attributes or contain nested child events. The event sets 606 are typically created based on an operator that selects certain events from the patient data stream stored in the longitudinal database 510. Examples of these operators are further discussed below with respect to FIG. 7.

In FIG. 7, a table 700 of operators 702 have an example syntax according to one embodiment is shown. Each operator 702 may return exactly one instance of a return type 704 supported by the variable scripting language unit 106. For example, the return type 704 can be, but not limited to, a Boolean (Bool), integer (Int), double (Float), a defined constant value (enum), etc. An operator 702 can take one or more inputs, such as the variable scripting language unit 106 data types (e.g., variables 602 and values 604 and event sets 606), inputs "t" for time or "D(t)" for a date range, as well as other symbolic constructs and other operators (e.g., and/or) to control the operator's behavior. In some embodiments, the operators 702 can be combined hierarchically (e.g., recursively) into a tree of operators to construct a value of interest. The root node operator of such a hierarchically tree represents a single instance of a patient variable expression and returns the event set from the longitudinal database 510 associated with a specified patient or patients. For example, using operator "PatientAttribute<T>(t)," where the operator may be used to reads a specified patient attribute value from the longitudinal data store on the given date. In some embodiments, there may be a determined set of "patient attributes" associated with each data set, such as gender, age, etc.) In one illustrative example, a user can create an variable expression to determine a patient or group of patients age over a time frame, such as the last 7 years, as Patient.Age(7), which may return an event set from the longitudinal database that includes the age of the patient at each year during the last 7 years, such as:

| Operator | Variable Name | Type | Time | | | | | | |
|---|---|---|---|---|---|---|---|---|---|
| | | | 1 | 2 | 3 | 4 | 5 | 6 | 7 |
| Patient.Age | Age | Int | 21 | 22 | 23 | 24 | 25 | 26 | 27 |

It should be appreciated that this is merely an illustrative example, as time granularity of the specified time frame returned by the operators 702 can be in days, weeks, months, years, etc.

Some other examples of operators may include the following: "First" is for determining the first time and event occurred within a time range, "Last" is for determining the last time and event occurred within a time range, "Exists" is for determining whether an event occurred within a time range, "AllEquals" is for determining whether an event occurred every day within a time range, "Collapse" is for nesting a set of related events together, "CountUnique" is for counting a number of distinct times an event occurred during a time range, "Sum" is for summing a number of distinct times an event occurred during a time range, "Extend" is for extending a number of days that an event occurred "Bound" is for setting a max/min boundary for the return values for an event, "Categorize" is for converting return values for an operator into an enum type, "Score" is for converting an enum return value of an operator into a number and "Flipped" is for flipping the return value of an operator, such as flipping true to false, as well as other types of operators are possible.

In some embodiments, once a patient variable expression is defined using a tree of operators with appropriate inputs, an aggregation can be applied to the variable expression to reduce a time varying sequence into a time series representing aggregated values for each day in the time series. One such aggregation may be to evaluate the variable expression on a single day or to calculate the sum of values over a range of days.

Given an expression where the patient variable of interest is defined as the root operator of that expression, the expression is evaluated by doing a bottom up evaluation of all operators in the tree until the root operator is evaluated to return a final value. While the same expression may be used for all patients, the final values may vary significantly based on the actual events in each patient data stream or attributes associated with the patients. Further examples of expressions and result sets using the variable scripting language unit 106 of system 100 can be found in the table below.

| Patient Data Sample | | | | | |
|---|---|---|---|---|---|
| | | | Time | | |
| Expression | Variable Name | Type | 1 | 2 | 3 |
| Patient.Age | Age | Integer | 21 | 22 | 23 |
| Patient.State | State | Category | NY | NY | FL |
| Last(Patient.State, Ever) State | Last Known | Category | NY | NY | NY |
| Patient.ZipCode | ZipCode | Category | 10022 | 10022 | 30527 |
| Patient.Gender | Gender | Category | Male | Male | Male |
| Patient.MaritalStatus | Marital Status | Category | Single | Single | Married |
| CMS.Outpatient Event/ MI.Occurrence | Patient MI Occurrence | Boolean | 0 | 1 | 0 |
| CMS.Measurement/BMI.Value | BMI Measurement | Double | 10000 | N/A | N/A |
| Active(CMS.Inpatient Event.Occurrence, duration = 3) | Beginning of Hospitalization | Boolean | 0 | 0 | 1 |
| Score(Obesity-N/A -> 0, Obesity-Normal -> 1, Obesity-Overweight -> 2) | Obesity Score | Integer | 0 | 0 | 0 |
| Active(CMS.Inpatient Event.Occurrence, duration = CMS.Inpatient Event.Duration) | Hospitalization | Boolean | 0 | 0 | 1 |
| Active(Laryngoscopy.Occurrence, duration = Laryngoscopy.Duration) | Laryngoscopy | Boolean | 0 | 0 | 0 |

-continued

Patient Data Sample

| Expression | Variable Name | Type | Time 1 | 2 | 3 |
|---|---|---|---|---|---|
| And(Beginning of Hospitalization, Serious Angioedema Complication) | Serious Angioedema Complication at the Beginning of Hospitalization | Boolean | 0 | 0 | 0 |

IV. Template Driven Reporting

Embodiments of the present disclosure provide intelligent reporting techniques that are capable of accessing the RCA functionality of system 100. In some embodiments, the intelligent reporting techniques are template driven and implement problem-based analytics for specific business use cases. A user may personalize some templates for certain studies while other templates may be enterprise wide templates used by a stakeholder or business unit. Each template may be used to solve a specific problem, e.g., identifying the patient sub-population that would benefit most from a specific treatment, based on patient events data stored in the longitudinal database of system 100.

Figure 8:
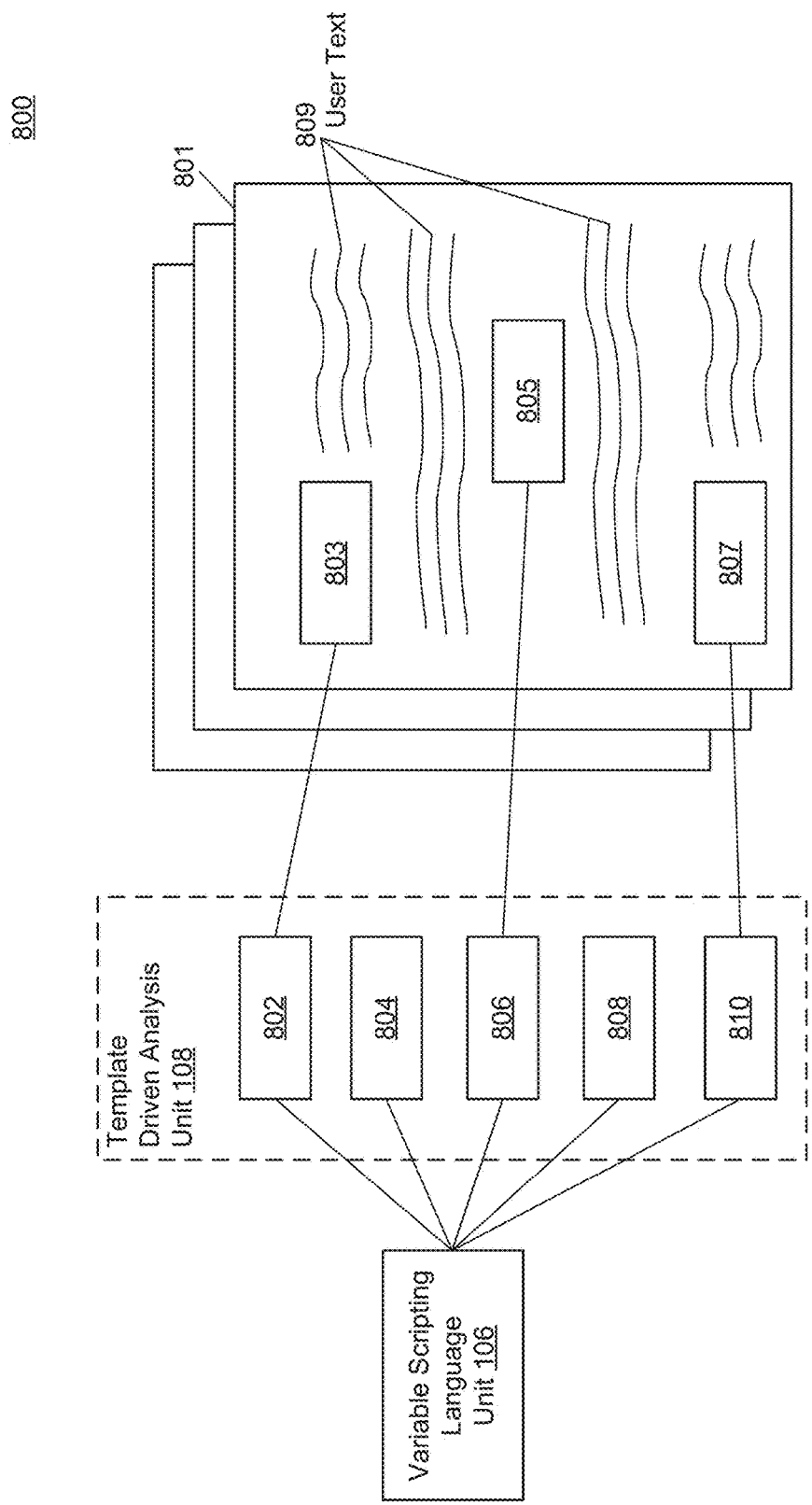
FIG. 8 illustrates a reporting system according to one embodiment.

FIG. 8 illustrates a reporting system 800 according to one embodiment is shown. The reporting system include a plurality of reports, such as report 801, based on templates, such as templates 802, 804, 806, 808 and 810, stored in the template driven analysis unit 108 of system 100. A user may use the template to prepare data for display by causing the template to perform expression queries against the longitudinal database of system 100. The user can enter text 809 that gets place in the appropriate places of the report 801. In some embodiments, the report 801 may be encoded with certain fields, such as fields 803, 805 and 807, which correspond to one of the templates 802, 804, 806, 808 and 810.

These fields may include variable expressions for generating queries against event data in longitudinal database. For example, an expression may be generated based on the variable data types associated with the variable scripting language unit 106. As noted above, the expression may comprise a set of operators that are adapted to evaluate a set of events (e.g., medical events) stored in the longitudinal database. The expressions may be used to retrieve values of interest to the report 801 from the longitudinal database. These values of interest may include, for example, predict outcomes (e.g., drug use trends, treatment outcomes) and other types of evidence-based analysis used in RCA.

After the values of interest are retrieved, the report 801 may be populated with related data associated with the values of interest. For example, event data as well as return values may be disposed into corresponding fields, such as fields 803, 805 and 807 of the report 801. Finalized reports are then delivered or retrieve by the user using, for example, the interface unit 102 of system 100.

V. Example Flow Diagrams

To better aid in understanding an example of some of the aspects of the present disclosure described above, for example, that are related to deriving a patient level longitudinal database for RCA, reference is now made to the following example flow diagrams. Operations described in flow diagrams can be performed by processing logic that can comprise hardware (e.g., circuitry, dedicated logic, programmable logic, microcode, etc.), software (e.g., instructions run on a processing device), or a combination thereof. It should be noted that the following operations do not have to be performed in the precise order described below. Rather, various operations can be handled in a different order or simultaneously, and some operations may be added or omitted.

Figure 9:
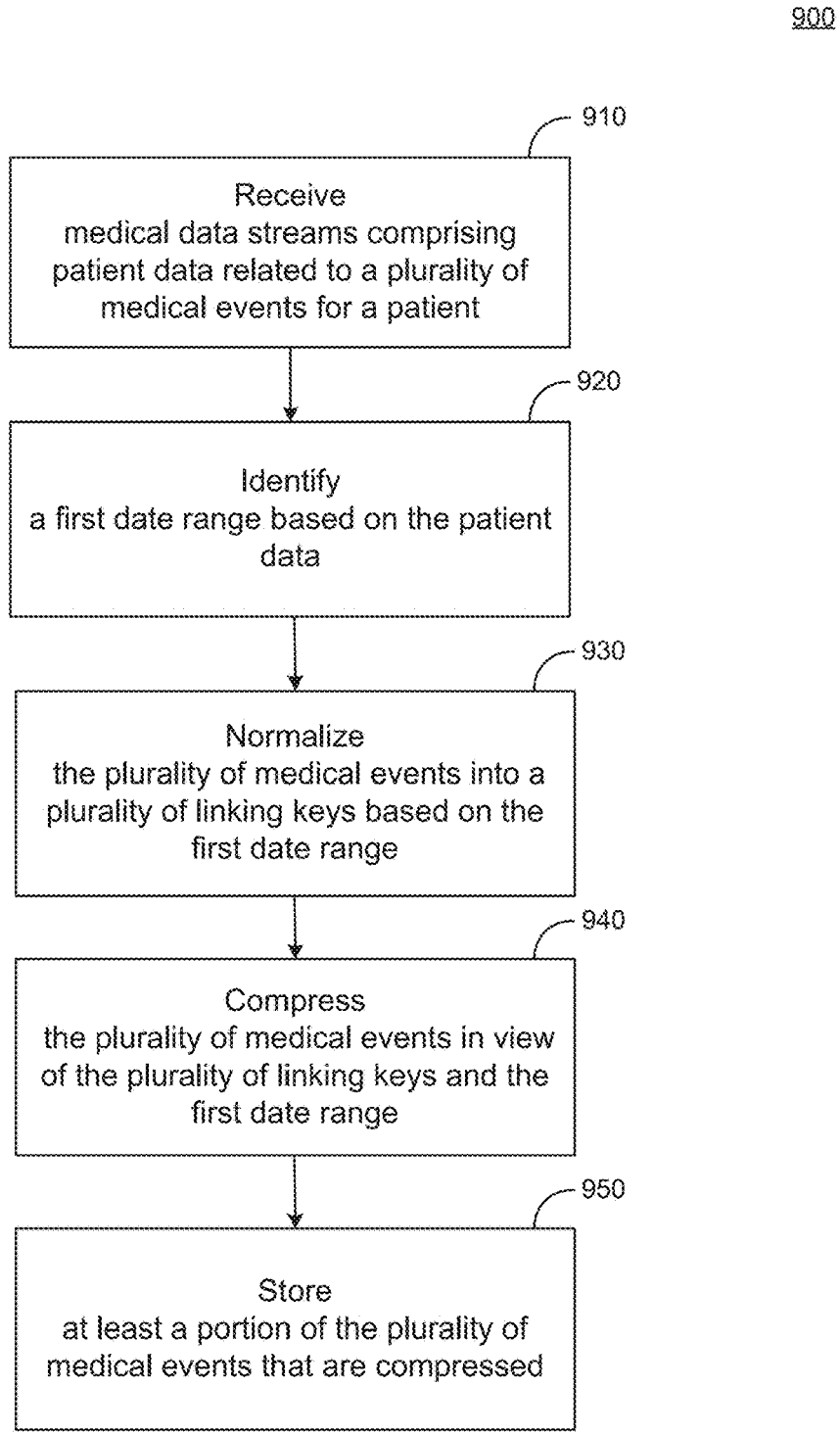
FIG. 9 illustrates a flow diagram of a method of assembling a longitudinal database according to one embodiment.

FIG. 9 illustrates a flow diagram of a method 900 of assembling a longitudinal database according to one embodiment. Method 900 may be performed by processing logic that may comprise hardware (e.g., circuitry, dedicated logic, programmable logic, microcode, etc.), software (such as instructions run on a processing device), firmware, or a combination thereof. In one embodiment, the longitudinal database generator 106 of the system 100 of FIG. 1 may perform method 900. Although shown in a particular sequence or order, unless otherwise specified, the order of the processes can be modified. Thus, the illustrated implementations should be understood only as examples, and the illustrated processes can be performed in a different order, and some processes may be performed in parallel. Additionally, one or more processes can be omitted in various embodiments. Thus, not all processes are required in every implementation. Other process flows are possible.

Method 900 begins at block 910 where medical data streams comprising patient data related to a plurality of medical events for a patient are received, for example, from a plurality of different sources. At block 920, a first date range is identified based on the patient data. The plurality of medical events are normalized or otherwise expanded into a plurality of linking keys based on the first date range in block 930. Then, the plurality of medical events in view of the plurality of linking keys and the first date range in block 940. At block 950, at least a portion of the compressed plurality of medical events is stored, for example, in a file of a file system.

Figure 10:
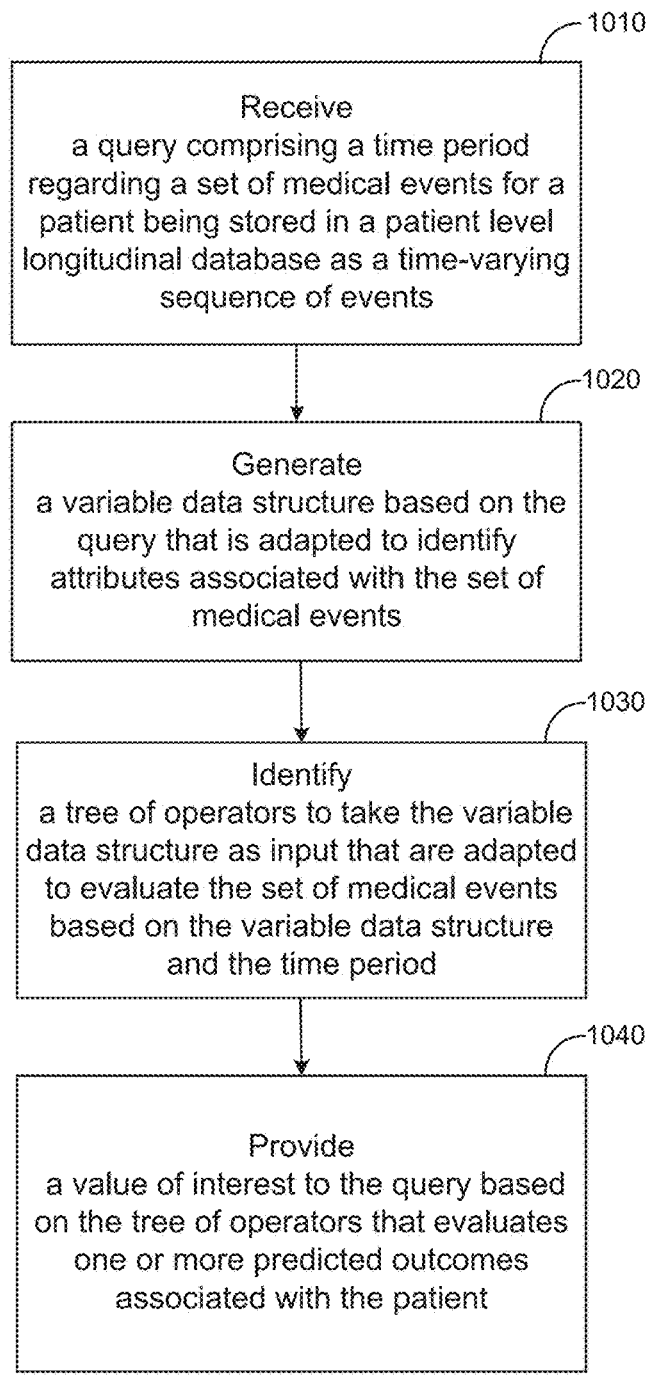
FIG. 10 illustrates a flow diagram of a method of analyzing patient level longitudinal event data according to one embodiment.

FIG. 10 illustrates a flow diagram of a method 1000 of analyzing patient level longitudinal event data according to one embodiment. Method 1000 may be performed by processing logic that may comprise hardware (e.g., circuitry, dedicated logic, programmable logic, microcode, etc.), software (such as instructions run on a processing device), firmware, or a combination thereof. In one embodiment, the variable scripting language unit 108 of the system 100 of FIG. 1 may perform method 1000. Although shown in a particular sequence or order, unless otherwise specified, the order of the processes can be modified. Thus, the illustrated implementations should be understood only as examples, and the illustrated processes can be performed in a different order, and some processes may be performed in parallel.

Additionally, one or more processes can be omitted in various embodiments. Thus, not all processes are required in every implementation. Other process flows are possible.

Method 1000 begins at block 1010 where a query is received comprising a time period regarding a set of medical events for a patient being stored in a patient level longitudinal database as a time-varying sequence of events. At block 1020, a variable data structure that is adapted to identify attributes associated with the set of medical events may be generated based on the query. At block 1030, a tree of operators may be identified to take the variable data structure as input. The tree of operators is adapted to evaluate the set of medical events based on the variable data structure and the time period. Thereafter, a value of interest to the query may be provided based on the tree of operators. The value of interest evaluates one or more predicted outcomes associated with the patient.

Figure 11:
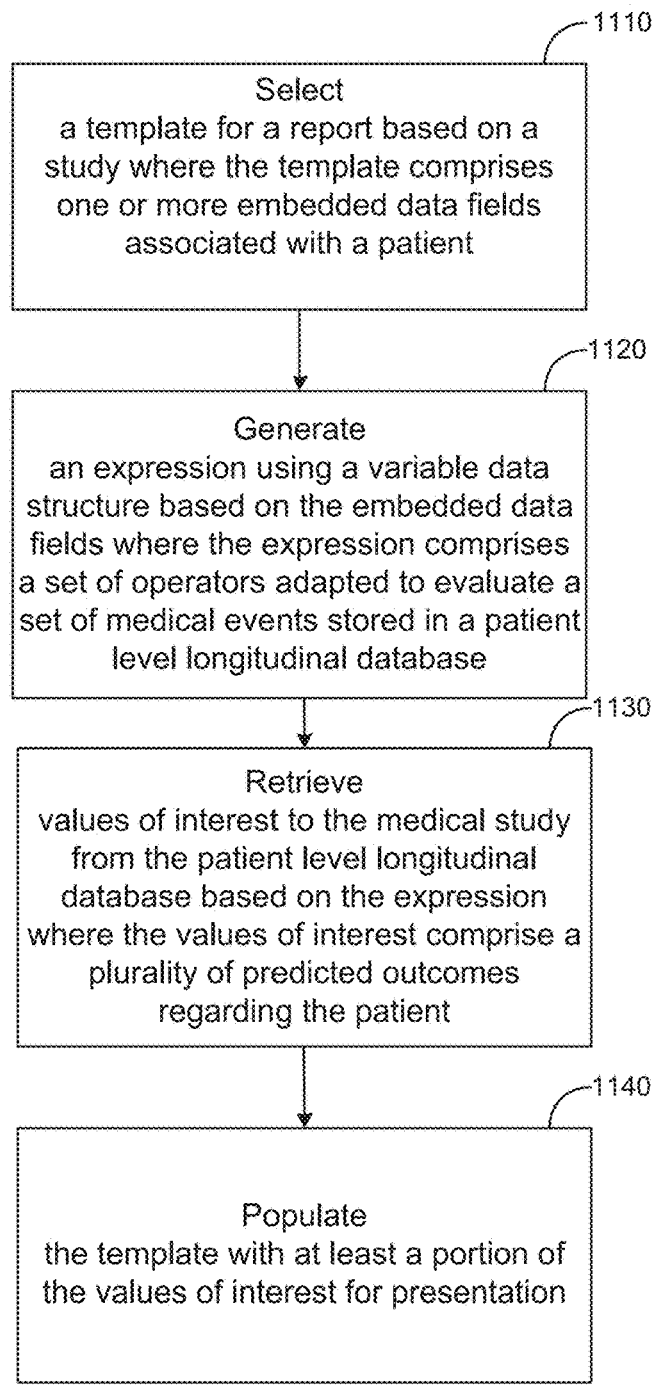
FIG. 11 illustrates a flow diagram of a method of generating template driven reports according to one embodiment.

FIG. 11 illustrates a flow diagram of a method 1100 of generating template driven reports according to one embodiment. Method 1100 may be performed by processing logic that may comprise hardware (e.g., circuitry, dedicated logic, programmable logic, microcode, etc.), software (such as instructions run on a processing device), firmware, or a combination thereof. In one embodiment, the template driven analysis unit 110 of the system 100 of FIG. 1 may perform method 1100. Although shown in a particular sequence or order, unless otherwise specified, the order of the processes can be modified. Thus, the illustrated implementations should be understood only as examples, and the illustrated processes can be performed in a different order, and some processes may be performed in parallel. Additionally, one or more processes can be omitted in various embodiments. Thus, not all processes are required in every implementation. Other process flows are possible.

Method 1100 begins at block 1110 where a template for a report is selected based on a study. The template comprises one or more embedded data fields associated with a patient. At block, 1120, an expression using a variable data structure may be generated based on the embedded data fields. The query comprises a set of operators adapted to evaluate a set of medical events stored in a patient level longitudinal database. At block 1130, values of interest to the medical study may be retrieved from the patient level longitudinal database based on the query. The values of interest comprise a plurality of predicted outcomes regarding the patient. Then, the template is populated with at least a portion of the values of interest for presentation at block 1140.

VI. Example Network

Implementations of the present disclosure may include a method for optimizing geometries on a machine, a system or apparatus as part of or in relation to the machine, or a computer program product embodied in a non-transitory computer readable medium executing on one or more of the machines. The one or more processors may be part of a server, client, network infrastructure, mobile computing platform, stationary computing platform, or other computing platform.

The algorithms and displays presented herein are not inherently related to a particular computer or other apparatus. Rather, various general-purpose systems can be used with programs in accordance with the teachings herein, or it may prove convenient to construct a more specialized apparatus to perform the method steps. The structure for a variety of these systems will appear from the description below. In addition, embodiments of the present invention are not described with reference to a particular programming language. It will be appreciated that a variety of programming languages can be used to implement the teachings of embodiments of the invention as described herein.

Unless specifically stated otherwise as apparent from the following discussion, it should be appreciated that throughout the description, discussions utilizing terms such as "initiating," "receiving," "generating," "providing," "sending," "detecting," "accessing," or the like, refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices.

Figure 12:
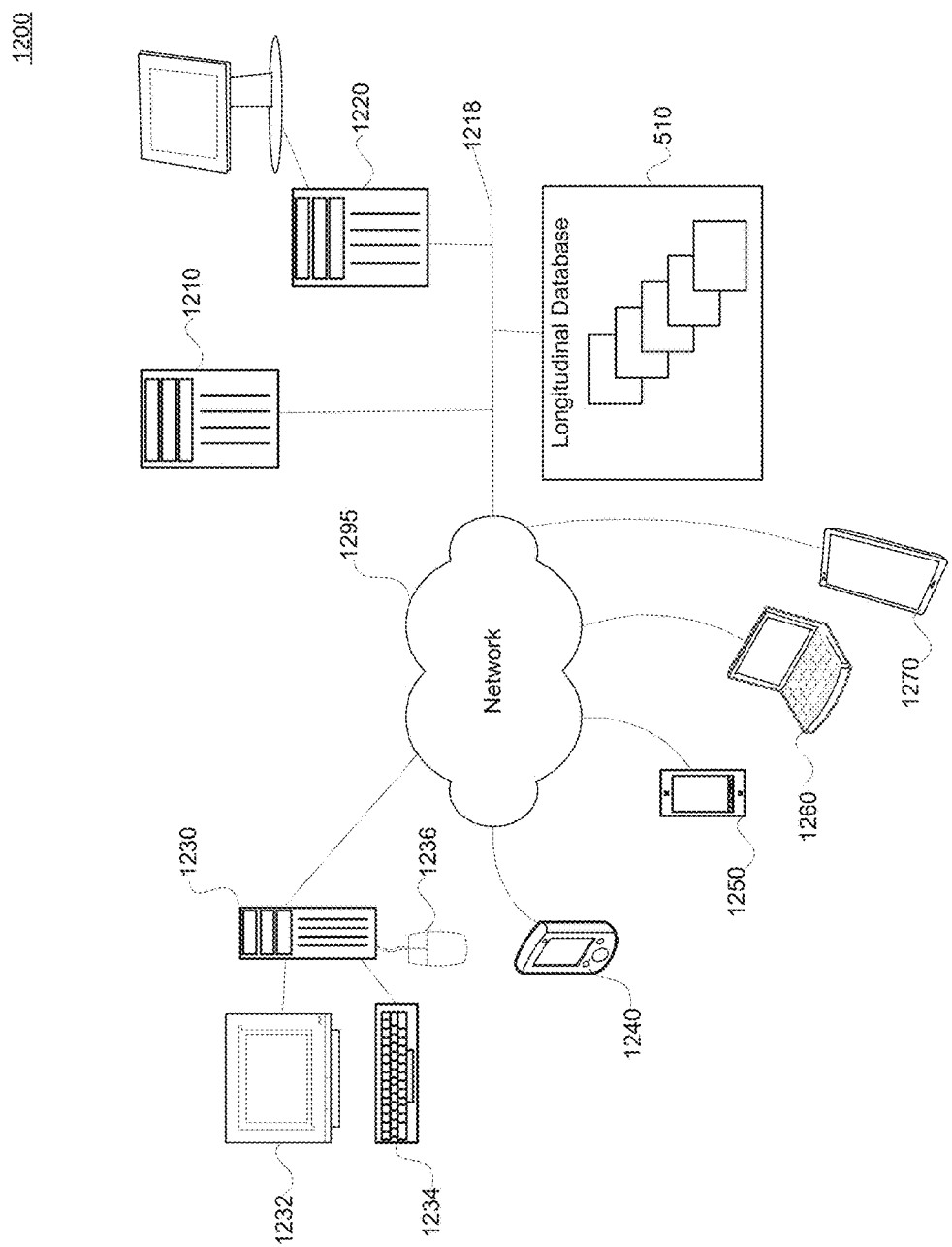
FIG. 12 is a block diagram illustrating a network in which an embodiment of the disclosure may be used.

FIG. 12 illustrates an exemplary computer network 1200 in which various implementations of the present disclosure may operate. As illustrated, computer network 1200 depicts various computing devices that can be used alone or in a networked configuration. For example, this figure of network 1200 illustrates a distributed computer network having a plurality of server computing devices 1210 and 1220 as well as various type of client computing devices, such as computer terminal 1230, PDA 1240, cellular phone 1250, laptop/net-book 1260 and tablet computer 1270 as well as other types of computing devices (not shown). These various devices may be interconnected via a local bus or direct connection 1218 and/or may be coupled via a communications network 220, which may be wired or wireless, such as a LAN, WAN, the Internet, etc.

Each device may include, for example, user input devices such as a keyboard 1234 and mouse 1236 and/or various other types of input devices such as pen-inputs, joysticks, buttons, touch screens, etc., as well as a display 1232 which could include, for instance, a CRT, LCD, plasma screen monitor, TV, projector, etc. Each device may be a personal computer, application server, etc. By way of example only, computing device 1230 may be a personal computer while computing device 1210 may be a server. Longitudinal databases, such as longitudinal database 510, may be accessible to one or more of the computing devices or other devices of network 1200.

VII. Example Computer System

Figure 13:
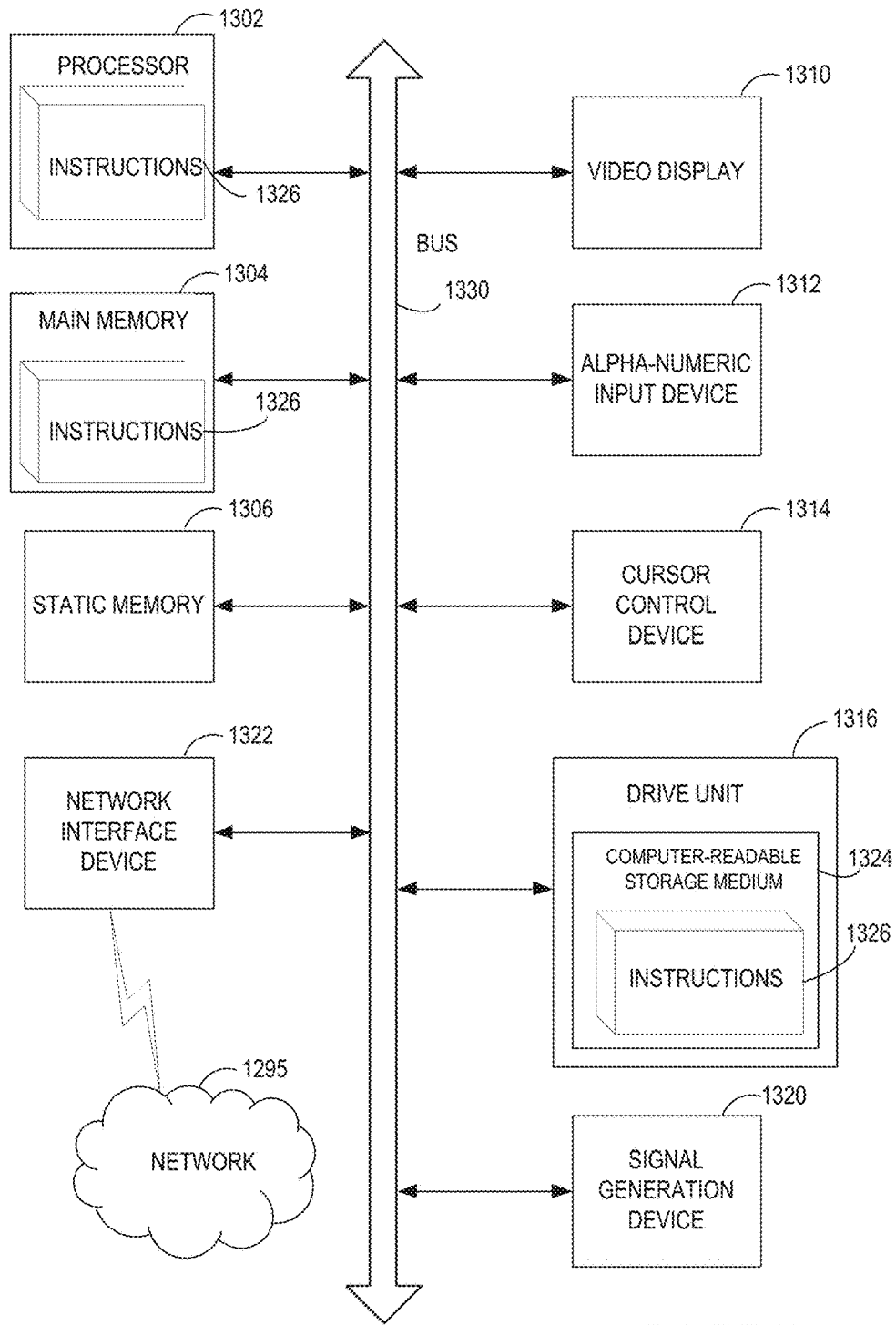
FIG. 13 illustrates a block diagram illustrating a computer system in which an embodiment of the disclosure may be used.

FIG. 13 is a block diagram illustrating a machine in the exemplary form of a computer system 1300 in accordance with various implementations. Within the computer system 1300 is a set of instructions for causing the machine to perform one or more of the methodologies discussed herein. In alternative embodiments, the machine may be connected (e.g., networked) to other machines in a LAN, an intranet, an extranet, or the Internet. The machine can operate in the capacity of a server or a client machine (e.g., a client computer executing the browser and the server computer executing the automated task delegation and project management) in a client-server network environment, or as a peer machine in a peer-to-peer (or distributed) network environment. The machine may be a personal computer (PC), a tablet PC, a console device or set-top box (STB), a Personal Digital Assistant (PDA), a cellular telephone, a web appliance, a server, a network router, switch or bridge, or a machine capable of executing a set of instructions (sequential or otherwise) that specify actions to be taken by that machine. Further, while only a single machine is illustrated, the term "machine" shall also be taken to include a collection of machines (e.g., computers) that individually or jointly execute a set (or multiple sets) of instructions to perform one or more of the methodologies discussed herein.

The computer system 1300 includes a processing device 1302 (e.g., a processor), a main memory 1304 (e.g., read-only memory (ROM), flash memory, dynamic random access memory (DRAM) such as synchronous DRAM (SDRAM) or DRAM (RDRAM), etc.), a static memory 1106 (e.g., flash memory, static random access memory (SRAM), etc.), and a secondary memory (e.g., a data storage device in the form of a drive unit 1316, which may include fixed or removable computer-readable storage medium), which communicate with each other via a bus 1330.

Processing device 1302 represents one or more general-purpose processors such as a microprocessor, central processing unit, or the like. More particularly, the processing device 1302 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processing device 702 may also be one or more special-purpose processing devices such as an application specific integrated circuit (ASIC), a field programmable gate array (FPGA), a digital signal processor (DSP), network processor, or the like. Processing device 1302 is configured to execute modules (e.g., longitudinal data generator 106, variable scripting language unit 108 and template driven analysis unit 110) of server 101 for performing the operations and steps discussed herein. For example, in one embodiment, flow diagrams 900, 1000 and 1100 may be performed by one or more of the modules.

The processing device 1302 may be capable of executing program instructions, codes, binary instructions and the like. The processor may include memory that stores methods, codes, instructions and programs as described herein and elsewhere. The processor may access a computer-readable storage medium through an interface that may store methods, codes, and instructions as described herein and elsewhere. The computer-readable storage medium associated with the processor for storing methods, programs, codes, program instructions or other type of instructions capable of being executed by the computing or processing device may include but may not be limited to one or more floppy diskettes, optical disks, Compact Disc, Read-Only Memory (CD-ROMs), and magneto-optical disks, Read-Only Memory (ROMs), Random Access Memory (RAM), Erasable Programmable Read-Only memory (EPROM), Electrically Erasable Programmable Read-Only Memory (EEPROM), magnetic or optical cards, flash memory, or the like.

The computer system 1300 may further include a network interface device 1322. The computer system 1300 also may include a video display unit 1310 (e.g., a liquid crystal display (LCD) or a cathode ray tube (CRT)) connected to the computer system 1300 through a graphics port and graphics chip-set, an alphanumeric input device 1312 (e.g., a keyboard), a cursor control device 1314 (e.g., a mouse), and a signal generation device 1320 (e.g., a speaker).

The drive unit 1316 or secondary memory may include a machine-readable storage medium (or more specifically a non-transitory computer-readable storage medium) 1324 on which is stored one or more sets of instructions 1326 embodying one or more of the methodologies or functions described herein. The sets of instructions 1326 may also reside, completely or at least partially, within the main memory 1304 and/or within the processing device 1304 during execution thereof by the computer system 1300, the main memory 1304 and the processing device 1302 also constituting machine-readable storage media. The sets of instructions 1326 may further be transmitted or received over a network 220 via the network interface device 1322.

The non-transitory computer-readable storage medium 1324 may also be used to store the modules of server 101 persistently. While the computer-readable storage medium 1324 is shown in as a single medium, the term "computer-readable storage medium" should be taken to include a single medium or multiple media (e.g., a centralized or distributed database, and/or associated caches and servers) that store the one or more sets of instructions. The terms "computer-readable storage medium" shall also be taken to include a medium that is capable of storing or encoding a set of instructions for execution by the machine and that cause the machine to perform one or more of the methodologies of the present invention. The term "computer-readable storage medium" shall accordingly be taken to include, but not be limited to, solid-state memories, and optical and magnetic media.

The computing system 1300, components and other features described herein can be implemented as discrete hardware components or integrated in the functionality of hardware components such as ASICS, FPGAs, DSPs or similar devices. In addition, aspects of the computing system 1300 can be implemented as firmware or functional circuitry within hardware devices. Further, the computing system 1300 can be implemented in a combination hardware devices and software components. For example, the functionality of this computing system 1300 can exist in a fewer or greater number of modules than what is shown, with such modules residing at one or more computing devices that may be geographically dispersed. The modules may be operable in conjunction with network 202 from which it may receive and provide relevant information regarding RCA.

Some portions of the above-disclosure are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of operations leading to a result. The operations are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the above description, numerous details are set forth. It will be apparent, however, to one skilled in the art, that the present disclosure may be practiced without these specific details. In some instances, well-known structures and devices are shown in block diagram form, rather than in detail, in order to avoid obscuring the present invention. In the foregoing, implementations of the present disclosure have been described with reference to specific example implementations thereof. The specification and drawings are to be regarded in an illustrative sense rather that a restrictive sense. It will be evident various modifications and combinations of the features discussed above can be utilized without departing from the disclosure as set forth in the following claims.

What is claimed is:

1. A method of assembling a longitudinal database, comprising:
    receiving, by a processing device of a data storage unit, medical data streams from a plurality of sources, the medical data streams comprising patient data related to a plurality of medical events for a patient;
    identifying a first date range indicating a time span associated with the patient in view of the patient data;
    transforming the medical data streams into a time-ordered data structure comprising a plurality of linking keys representing a time-ordered sequence of the plurality of medical events for the patient corresponding to the first date range;
    expanding, by the processing device, the plurality of linking keys based on the first date range and location information associated with an occurrence of a corresponding medical event, wherein each of the plurality of linking keys corresponds to a date within the first date range, wherein a first linking key of the plurality of linking keys comprises a first offset value representing a number of days between a start date of the first date range and a first medical event associated with the first linking key;
    compressing, by the processing device, the plurality of linking keys to generate a temporal location index for each of the medical events associated with the plurality of linking keys; and
    facilitating a search of the temporal location index to identify the first medical event and first temporal location of the first medical event.

2. The method of claim 1, wherein the temporal location index indicates a temporal location of a corresponding medical event within the first date range.

3. The method of claim 1, wherein the data storage unit comprises a file system and at least a portion of the plurality of medical events that is compressed is stored in an encrypted file of the file system.

4. The method of claim 1, wherein expanding comprises:
    storing medical events from the plurality of medical events at a corresponding linking key.

5. The method of claim 4, wherein a date of occurrence for a medical event stored at a linking key corresponds to a date associated with the linking key.

6. The method of claim 5, wherein an offset of the linking key associated with the medical event comprises a difference between the date of occurrence for the medical event and the start date of the first date range.

7. The method of claim 1, wherein compressing further comprises generating a plurality of metadata for each medical event of the plurality of medical events, each metadata of the plurality of metadata indicating a temporal location within the first date range for longitudinally transitioning from a first medical event to a second medical event associated with the plurality of medical events.

8. The method of claim 1, further comprising:
    storing an indication associated with an end date of the first date range;
    identifying a second date range based on other patient data for the patient; and
    updating the plurality of medical events stored at the data storage unit with compressed medical events data associated with the other patient data in view of the indication and the second date range.

9. A system comprising:
    a memory device for storing medical events; and
    a processing device coupled to the memory device, the processing device is to:
    receive medical data streams from a plurality of sources, the medical data streams comprising patient data related to a plurality of medical events for a patient;
    identify a first date range indicating a time span associated with the patient in view of the patient data;
    transform the medical data streams into a time-ordered data structure comprising a plurality of linking keys representing a time-ordered sequence of the plurality of medical events for the patient corresponding to the first date range;
    expand the plurality of linking keys based on the first date range and location information associated with an occurrence of a corresponding medical event, wherein each of the plurality of linking keys corresponds to a date within the first date range, wherein a first linking key of the plurality of linking keys comprises a first offset value representing a number of days between a start date of the first date range and a first medical event associated with the first linking key;
    compress the plurality of linking keys to generate a temporal location index for each of the medical events associated with the plurality of linking keys; and
    facilitate a search of the temporal location index to identify the first medical event and first temporal location of the first medical event.

10. The method of claim 9, wherein the temporal location index indicates a temporal location of a corresponding medical event within the first date range.

11. The system of claim 9, wherein the memory device comprises a file system and at least a portion of the plurality of medical events that is compressed is stored in an encrypted file of the file system.

12. The system of claim 9, wherein to expand the processing device is further to:
    store medical events from the plurality of medical events at a corresponding linking key.

13. The system of claim 12, wherein a date of occurrence for a medical event stored at a linking key corresponds to a date associated with the linking key.

14. The system of claim 13, wherein an offset of the linking key associated with the medical event comprises a difference between the date of occurrence for the medical event and the start date of the first date range.

15. The system of claim 9, wherein to compress the processing device is further to generate a plurality of metadata for each medical event of the plurality of medical events, each metadata of the plurality of metadata indicating a temporal location within the first date range for longitudinally transitioning from a first medical event to a second medical event associated with the plurality of medical events.

16. The system of claim 9, wherein the processing device is further to:
    store an indication associated with an end date of the first date range;
    identify a second date range based on other patient data for the patient; and
    update the plurality of medical events stored at the data storage unit with compressed medical events data associated with the other patient data in view of the indication and the second date range.

17. A non-transitory computer-readable storage medium comprising executable instructions that, when executed by a processing device, cause the processing device to:
receive, by the processing device, medical data streams from a plurality of sources, the medical data streams comprising patient data related to a plurality of medical events for a patient;
identify a first date range indicating a time span associated with the patient in view of the patient data;
transform the medical data streams into a time-ordered data structure comprising a plurality of linking keys representing a time-ordered sequence of the plurality of medical events for the patient corresponding to the first date range;
expand the plurality of linking keys based on the first date range and location information associated with an occurrence of a corresponding medical event, wherein each of the plurality of linking keys corresponds to a date within the first date range, wherein a first linking key of the plurality of linking keys comprises a first offset value representing a number of days between a start date of the first date range and a first medical event associated with the first linking key;
compress the plurality of linking keys to generate a temporal location index for each of the medical events associated with the plurality of linking keys; and
facilitate a search of the temporal location index to identify the first medical event and first temporal location of the first medical event.

18. The method of claim 17, wherein the temporal location index indicates a temporal location of a corresponding medical event within the first date range.

19. The non-transitory computer-readable storage medium of claim 17, wherein at least a portion of the plurality of medical events that is compressed is stored in an encrypted file of a file system.

20. The non-transitory computer-readable storage medium of claim 17, wherein to expand the executable instructions further cause the processing device to:
store medical events from the plurality of medical events at a corresponding linking key of the plurality of linking keys.

* * * * *